United States Patent
Kath et al.

(10) Patent No.: US 7,122,670 B2
(45) Date of Patent: Oct. 17, 2006

(54) SELECTIVE SYNTHESIS OF CF3-SUBSTITUTED PYRIMIDINES

(75) Inventors: John Charles Kath, Waterford, CT (US); Daniel Tyler Richter, Groton, CT (US); Michael Joseph Luzzio, Noank, CT (US)

(73) Assignee: Pfizer Inc, New York, NY (US)

( * ) Notice: Subject to any disclaimer, the term of this patent is extended or adjusted under 35 U.S.C. 154(b) by 217 days.

(21) Appl. No.: 10/928,954

(22) Filed: Aug. 27, 2004

(65) Prior Publication Data

US 2005/0101620 A1    May 12, 2005

Related U.S. Application Data

(60) Provisional application No. 60/500,733, filed on Sep. 5, 2003.

(51) Int. Cl.
| | |
|---|---|
| *C07D 239/42* | (2006.01) |
| *C07D 239/48* | (2006.01) |
| *A61K 31/505* | (2006.01) |
| *A61K 31/506* | (2006.01) |
| *A61P 35/00* | (2006.01) |

(52) U.S. Cl. ................. 544/330; 544/331; 544/324; 514/275

(58) Field of Classification Search ............... 544/330, 544/331
See application file for complete search history.

(56) References Cited

FOREIGN PATENT DOCUMENTS

WO        03030909        4/2003

OTHER PUBLICATIONS

Diringer et al., Journal of Medicinal Chemistry, vol. 13, No. 1, pp. 151-152 (1970).

*Primary Examiner*—Venkataraman Balasubramanian
(74) *Attorney, Agent, or Firm*—Steven Zelson; David L. Kershner

(57) ABSTRACT

The present invention relates to a method of making a compound of the formula

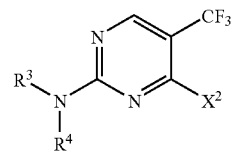

wherein $X^1$, $X^2$ and $R^3$—$R^4$ are as defined herein. The method includes reacting a compound of the formula

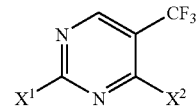

with an amine of formula 3 ($HNR^3R^4$) in the presence of a Lewis Acid and a non-nucleophilic base. The 2,4-diamino pyrimidine moiety is a common component in a variety of biologically active drug-like molecules and pyrimidine derivatives have been found to be useful in the treatment of abnormal cell growth, such as cancer, in mammals.

14 Claims, No Drawings

SELECTIVE SYNTHESIS OF CF3-SUBSTITUTED PYRIMIDINES

CROSS-REFERENCE TO RELATED APPLICATIONS

Reference is made to U.S. Application Ser. No. 60/500,733, filed Sep. 5, 2003, the disclosure of which is incorporated herein by reference in its entirety.

BACKGROUND OF THE INVENTION

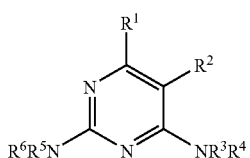

The 2,4-diamino pyrimidine moiety (1) is a common component in a variety of biologically active drug-like molecules. Pyrimidine derivatives have been found to be useful in the treatment of abnormal cell growth, such as cancer, in mammals. These moieties are commonly synthesized starting with pyrimidine intermediate 2 (where "X" is a leaving group; most commonly a halogen) and an equivalent of amine 3, $HNR^3R^4$ (see Scheme 1 below). For the vast majority of reactions involving pyrimidines of formula 2 and amines of formula 3, it is well known that this first amine addition occurs preferentially (or exclusively) at the more reactive pyrimidine 4-position (*Chemistry of Heterocyclic Compounds, The Pyrimidines*, Volume 52, Wiley, New York 1994, p. 371.) to provide intermediate 4. The primary factors that influence the selectivity of this initial amine addition are the stereoelectronic effects associated with substituents present in both pyrimidine 2 and amine 3 and to a lesser extent the reaction solvent. Subsequent heating of 4 with a second amine (5) provides the desired 2,4-diaminopyrimidine 1.

SCHEME 1

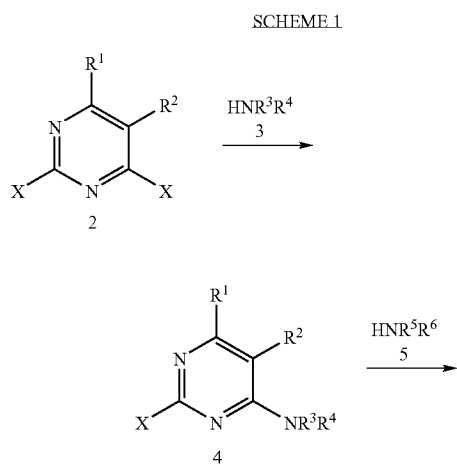

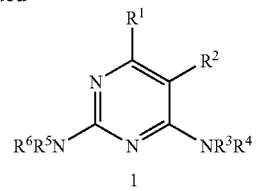

A representative example of the aforementioned chemistry can be found in WO00391901 and is highlighted in Scheme 2. Other examples utilizing this general synthetic scheme include Montebugnoli et. al. Tetrahedron 2002, (58), p. 2147. *Chemistry of Heterocyclic Compounds, The Pyrimidines*, Volume 52, Wiley, New York 1994, pp. 371–417. Selective amine addition to 2,4-dichloro-5-carboxamidopyrimidines is described in WO 02/04429. Selective amine additions to 2,4-dichloro-5-halopyrimidines are described in WO 01/65655.

SCHEME 2

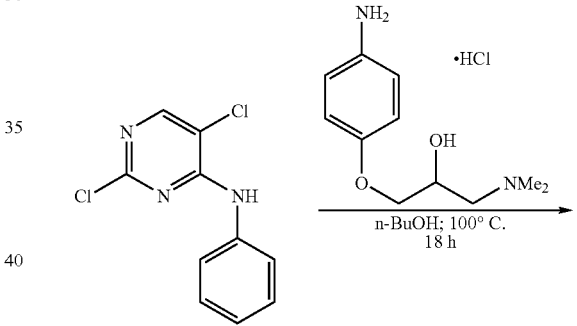

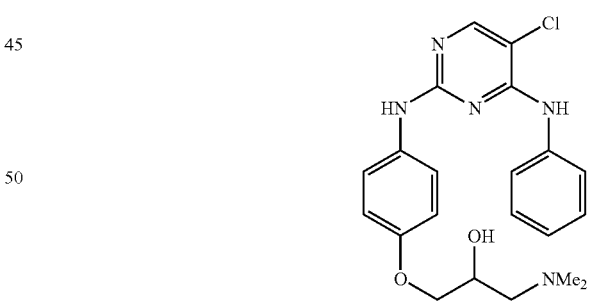

While there are a number of general examples where specific pyrimidines (2), amines (3) or reaction conditions provide non-selective mixtures of the 2-chloro-4-aminopyrimidine (4) and the isomeric 2-amino-4-chloro-pyrimidine (6) (Scheme 3), these reactions are of limited utility not only due to their lack of selectivity (and its impact on overall yield) but also because separation of the resulting isomers is generally extremely difficult. Preparative HPLC is generally required as a means to individually isolate the pure isomers (4 and 6), which can then be transformed further into compounds such as 1 or its isomer 7 respectively.

SCHEME 3

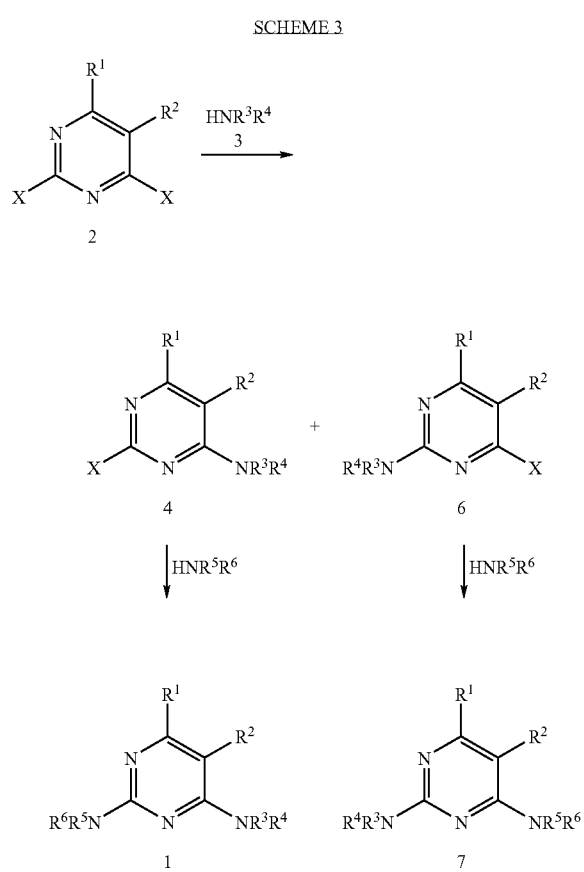

An example of such a reaction that provides mixtures of isomers is the addition of 4-methyl-aniline to 2,4-dichloro-5-trifluoromethylpyrimidine (Scheme 4). This electron deficient pyrimidine has a slight preference for amine addition to the pyrimidine 2-position. HPLC analysis of the crude reaction mixture shows a 1.4 to 1 mixture of and (4-Chloro-5-trifluoromethyl-pyrimidin-2-yl)-p-tolyl-amine (8) and (2-Chloro-5-trifluoromethyl-pyrimidin-4-yl)-p-tolyl-amine (9). Other examples of non-selective amine addition to 2,4 di-halogenopyrimidines are described in *Chemistry of Heterocyclic Compounds, The Pyrimidines*, Volume 52, Wiley, New York 1994, pp. 371–417. Luo et. al. Tetrahedron Lett. 2002, (43) p. 5739. Yoshida et. al. *J. Chem. Soc, Perkin Trans. 1: Organic and Bioorganic Chemistry*, 1992 (7) p. 919. EP 647639 describes additions of piperidines to 2,4-dichloropyrimidine.

SCHEME 4

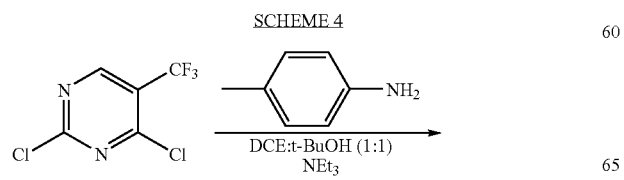

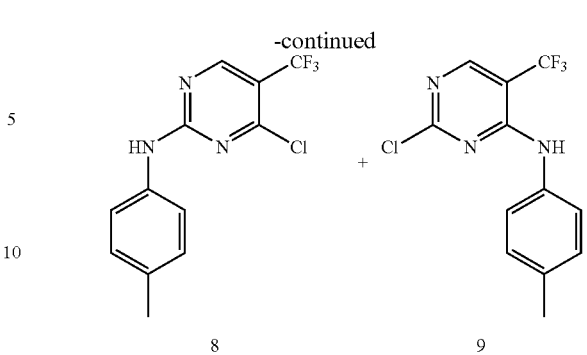

In contrast to the reactions described above, there are only a few very specific examples where an amine (3) is added to a pyrimidine of formula 2 in a selective manner to provide preferentially the 2-amino-4-chloro-pyrimidine 6. The most notable example of this type of reaction is the addition of N-methyl piperidine to 2,4-dichloro-5-methyl pyrimidine to provide 4-chloro-5-methyl-2-piperidinopyrimidine (Scheme 5) found in Yoshida et. al. *J. Chem. Soc, Perkin Trans. 1: Organic and Bioorganic Chemistry*, 1992 (7) p. 919. In this case, the steric effect of the 5-methyl substituent on the pyrimidine coupled with the fact that the amine nucleophile is a tertiary (rather than a primary or secondary) amine provides for selective addition of piperidine to the pyrimidine 2-position.

SCHEME 5

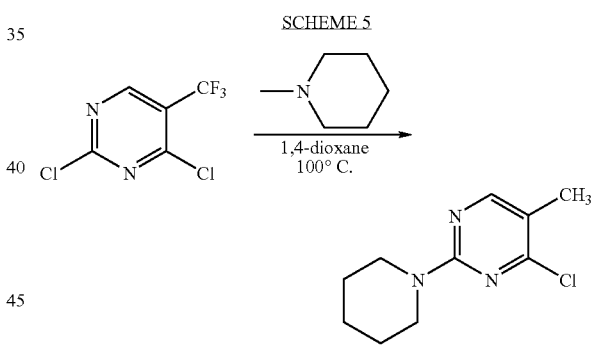

SUMMARY OF THE INVENTION

It has been surprisingly found that by adding a Lewis acid to the reaction medium, one can selectively add an amine functionality to the C-2 position of a $CF_3$ substituted-pyrimidine ring. Thus, the present invention relates to a process of making a compound of the formula 11

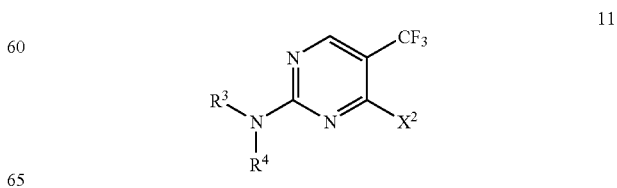

wherein $X^2$ is a leaving group such as a halide, arylsulfonate, alkylsulfonate, perfluoroalkylsulfonate, arylsulfinate or alkylsulfinate; and $R^3$ and $R^4$ are substituents independently selected from the group consisting of hydrogen, an aromatic group and an aliphatic group; or taken together —$NR^3R^4$ can form a 4–11 membered aromatic or aliphatic ring;

wherein the process comprises reacting a compound of formula 10

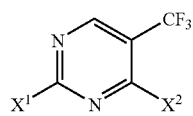

with an amine of formula 3 ($HNR^3R^4$) in the presence of a Lewis Acid and a non-nucleophilic base to form a compound of formula 11, wherein $X^1$ is a leaving group such as a halide, arylsulfonate, alkylsulfonate, perfluoroalkylsulfonate, arylsulfinate or alkylsulfinate.

In a preferred embodiment, amine 3 is an aromatic amine and 0.25–10 equivalents of Lewis Acid are used relative to the amount of pyrimidine 10, and preferably 0.5–3.0 equivalents of Lewis Acid are used relative to pyrimidine 10.

In an alternative preferred embodiment, amine 3 is an aliphatic amine and 0.5–10 equivalents of Lewis Acid are used relative to the amount of pyrimidine 10, and preferably 1–4 equivalents of Lewis Acid are used relative to pyrimidine 10.

In a further preferred embodiment, $X^1$ and $X^2$ are the same or different and are each independently halides and the Lewis Acid is a salt of zinc or magnesium.

In the most preferred embodiment, $X^1$ and $X^2$ are chloride and the Lewis Acid is zinc chloride The compounds prepared by the method of the present invention include all stereoisomers (e.g., cis and trans isomers) and all optical isomers of compounds of the formula 11 (e.g., R and S enantiomers), as well as racemic, diastereomeric and other mixtures of such isomers.

The compounds and salts prepared by the method of the present invention can exist in several tautomeric forms, including the enol and imine form, and the keto and enamine form and geometric isomers and mixtures thereof. The preparation of all such tautomeric forms is included within the scope of the present invention. Tautomers exist as mixtures of a tautomeric set in solution. In solid form, usually one tautomer predominates. Even though the preparation of one tautomer may be described, the present invention encompasses the preparation of all tautomers of the present compounds.

The present invention also includes the preparation of atropisomers of the present invention. Atropisomers refer to compounds of formula 11 that can be separated into rotationally restricted isomers.

The compounds prepared by the method of the invention may contain olefin-like double bonds. When such bonds are present, the compounds exist as cis and trans configurations and as mixtures thereof and the present invention contemplates the preparation of such compounds.

As used herein the term "aromatic", and specifically, an "aromatic group" refers to an aryl or heteroaryl radical as defined herein.

Further, an "aromatic amine" or "aromatic amine radical" refers to any amine or amine radical bound to at least one $sp^2$ carbon atom that is part of an aryl or heteroaryl group. An amine or amine radical will be referred to as an aromatic amine or radical even if the amine nitrogen is bound to a hydrogen or an $sp^3$ carbon atom, in addition to the one $sp^2$ carbon atom. Thus, for example, —$HN(C_6$–$C_{10})$aryl and —$N((C_1$–$C_6)$alkyl)$((C_6$–$C_{10})$aryl) each refer to aromatic amine radicals as defined herein, despite the fact that each amine nitrogen is attached to non-aromatic substituents.

The term "aryl" refers to aromatic radicals such as phenyl, naphthyl, tetrahydronaphthyl, indanyl and the like. An "aryl" group may be optionally substituted with 1–3 suitable substituents, as defined herein. "Aryl" also refers to a phenyl radical fused to a non-aromatic heterocycle. Examples of such groups include but are not limited to 2-oxbindolinyl, chromanyl, indolinyl and 2-oxo-3,4-dihydroquinolinyl optionally substituted by 1 to 3 suitable substituents.

As used herein, the term "heteroaryl" refers to an aromatic heterocyclic group usually with one heteroatom selected from O, S and N in the ring, wherein the aromatic heterocyclic group may be substituted by up to three suitable substituents as defined herein. In addition to said one heteroatom, the aromatic heterocyclic group may optionally have up to four N atoms in the ring. Examples of heteroaryl groups include but are not limited to pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like; optionally substituted by 1 to 3 suitable substituents. Alternatively, any ring carbon, —CH—, of the aforementioned heteroaryl group, may be replaced by a group selected from —C=O or —$SO_2$. "Heteroaryl" also refers to one of the aforementioned heteroaryl groups fused to a non-aromatic heterocycle. Examples of such groups include but are not limited to 1,3-Dihydro-pyrrolo[2,3-b]pyridin-2-one, 3,4-Dihydro-1H-[1,8]naphthyridin-2-one, 1,3-Dihydro-pyrrolo[2,3-b]pyridine and 3,4-Dihydro-2H-pyrano[2,3-b]pyridine.

"Aliphatic group" refers to an alkyl, cycloalkyl, or heterocycloalkyl radical, as defined herein. Aliphatic groups may be substituted with up to three suitable substituents as defined herein.

As used herein, the term "aliphatic amine" or "aliphatic amino radical" refers to any amine or amine radical in which the amine or radical nitrogen atom is bound to an $sp^3$ carbon that is part of an alkyl, cycloalkyl, or heterocycloalkyl group. Aliphatic amine groups may be substituted with up to three suitable substituents as defined herein.

The term "alkyl" refers to $C_1$–$C_{10}$ linear or branched alkyl groups (such as methyl, ethyl, n-propyl, isopropyl, n-butyl, isobutyl, sec-butyl, tert-butyl etc.) optionally substituted by 1 to 3 suitable substituents as defined herein.

The term "cycloalkyl" or "cyclyl" refers to $C_3$–$C_{12}$ mono, bicyclic or tricyclic carbocyclic ring (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.) that is optionally substituted by 1 to 3 suitable substituents as defined herein. Bicyclic or tricyclic species may be fused, bridged or spirocyclic. Thus, examples of "cycloalkyl" or "cyclyl" groups, as defined herein, include, but are not limited to cyclopropyl, cyclobutyl, cyclopentyl, cyclohexyl, cycloheptyl, cyclohexenyl, bicyclo[2.2.1]heptanyl, bicyclo[3.2.1]octanyl, bicyclo[3.1.0]hexyl and spiro[2.4]heptyl.

The term "heterocycloalkyl" or "heterocyclyl" or "heterocycle" refers to a mono, bicyclic or tricyclic group containing 3 to 9 carbon atoms and 1 to 4 heteroatoms selected from —N, —NR, —O—, —S—, —SO or —SO$_2$, wherein the cyclic radical is optionally substituted by 1 to 3 suitable substituents as defined herein. Bicyclic or tricyclic species may be fused, bridged or spirocyclic. Examples of such groups include but are not limited to azetidinyl, pyrrolidinyl, piperidinyl, morpholinyl, piperazinyl, tetrahydrofuranyl, oxetanyl, thiomorpholinyl, quinuclidinyl, 5-azaspiro[2.4]heptyl and 3-aza-bicyclo[3.1.0]hexyl.

As used herein, the term "halogen" includes fluoro, chloro, bromo or iodo or fluoride, chloride, bromide or iodide.

As used herein, the term "carbonyl" or "(C=O)" (as used in phrases such as alkylcarbonyl, alkyl-(C=O)— or alkoxycarbonyl) refers to the joinder of the >C=O moiety to a second moiety such as an alkyl or amino group (i.e. an amido group).

When —NR$^3$R$^4$ or —NR$^5$R$^6$ taken together form a cyclic amine, said amine can be a mono, bicyclic or tricyclic ring comprising 3 to 9 carbon atoms and 0 to 3 heteroatoms selected from —N, —O—, —S—, —SO or —SO$_2$ (excluding the nitrogen atom in —NR$^3$R$^4$ or —NR$^5$R$^6$). The cyclic amine may be optionally substituted with 1 to 3 suitable substituents as defined herein. Bicyclic or tricyclic species may be fused bridged or spirocyclic. Examples of such cyclic amines include but are not limited to morpholine, azetidine, piperazine, piperidine, pyrrolidine, indoline, thiomorpholine.

A "suitable substituent" is intended to mean a chemically and pharmaceutically acceptable functional group. Such suitable substituents for the aforementioned aryl, heteroaryl, alkyl, cycloalkyl, heterocycloalkyl groups may be routinely described by those skilled in the art. Illustrative examples of said suitable substituents include, but are not limited to hydrogen, halo groups, perfluoroalkyl groups, perfluoroalkoxy groups, alkyl groups, alkenyl groups, alkynyl groups, hydroxy groups, oxo groups, alkylthio groups, arylthio groups, alkylsulfonyl groups, arylsulfonyl groups, heteroarylsulfonyl groups, alkylsulfonate groups, arylsulfonate groups, perfluoroalkylsulfonate groups, alkoxy groups, aryl or heteroaryl groups, cycloalkyl or heterocycloalkyl groups, aryloxy or heteroaryloxy groups, aralkyl or heteroaralkyl groups, aralkoxy or heteroaralkoxy groups, HO—(C=O)— groups, amino groups, alkyl- and dialkylamino groups, carbamoyl groups, alkylcarbonyl groups, alkoxycarbonyl groups, alkylaminocarbonyl groups dialkylamino carbonyl groups, sulfonamido groups, alkylsulfonamido groups, dialkylsulfonamido groups, amido groups, N-acyl groups, arylcarbonyl groups, aryloxycarbonyl groups and the like. Methylene groups may also be substituted for a carbonyl (C=O) group. Those skilled in the art will appreciate that many substituents can be substituted by additional substituents.

"Embodiment" as used herein refers to specific groupings of compounds or uses into discrete subgenera. Such subgenera may be cognizable according to one particular substituent such as a specific R$^3$ or R$^4$ group. Other subgenera are cognizable according to combinations of various substituents, such as all compounds wherein R$^3$ is hydrogen and R$^4$ is (C$_1$–C$_6$)alkyl, optionally substituted by —(C$_3$–C$_{10}$) cyclyl.

DETAILED DESCRIPTION OF THE INVENTION

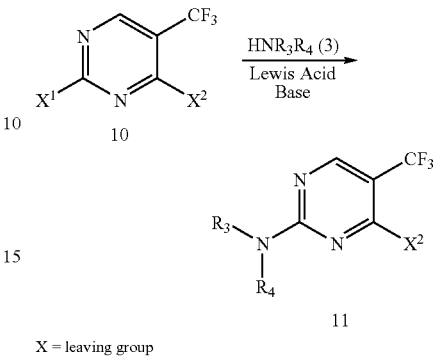

X = leaving group

Compounds of the formula 11 can be prepared by reaction of pyrimidine 10 and a primary or secondary amine nucleophile (3) in the presence of a Lewis acid and a non-nucleophilic base in an organic solvent or mixture of solvents. Leaving groups (X$^1$, X$^2$, which may be the same or different) on pyrimidine 10 suitable for displacement, include but are not limited to halides, sulfonates and sulfinates. Preferentially, each leaving group is a halide. In a further preferred embodiment, the halide is chloride. Suitable primary and secondary amine nucleophiles include aromatic, aliphatic or cyclic amines as described above. Lewis acids include but are not limited to the salts of Zn, Mg, Sn, Ti, Al, B, Li, Ag, Na, K, Ca, Va, Cr, Mn, Fe, Co, Ni, In, Zr, Sm and Cu. In a preferred embodiment, salts of Zn, Mg, Sn, Ti, Al, B, Li, Ag, and Cu are preferred. Most preferably, a salt of Zn or Mg is used as the Lewis acid. Suitable equivalents of Lewis Acid relative to pyrimidine 10 necessary to effect selective amine addition range from 0.25–10 equivalents, and preferably 0.5–3 equivalents when the amine nucleophile is aromatic or 0.5–10 equivalents, and preferably 1–4 equivalents when the amine is aliphatic (or an aromatic amine capable of forming a multidentate ligand with the Lewis Acid). Suitable organic solvents include but are not limited tetrahydrofuran, 1,2-dichloroethane, t-butanol, ether, methylene chloride, acetonitrile, methanol, ethanol, 2-propanol, dioxane, 1,2-dimethoxyethane, toluene, chloroform, ethyl acetate or mixtures thereof, preferably a mixture of a halogenated and alcoholic solvents. Suitable non-nucleophilic bases include but are not limited to triethylamine, N,N-diisopropyl-ethylamine, diaza-bicyloundecene (DBU) or resin bound bases such as MP-Carbonate. Temperatures for this process range from –30° C. to 50° C.; preferably the reaction is run at 0° C. to room temperature.

The reaction may be carried out in a single step or in several sequential steps, without any adverse effect on the overall yield or selectivity of the reaction.

Compounds of the formula 11, when combined with a primary or secondary amine HNR$^5$R$^6$ (5) are useful in the preparation of compounds of formula 12, where R$^5$ and R$^6$ independently represent hydrogen, an aromatic group or an aliphatic group, or NR$^5$R$^6$ taken together can form a 4–11 membered aromatic or aliphatic ring. Alternatively, compounds of formula 11 are useful in the preparation of compounds of formula 13a or 13b by addition of an oxygen or sulfur nucleophile, respectively. Compounds of formula 11 (where X is a halide or perfluoroalkylsulfonate) are also useful in preparing compounds of formula 14 or 15a/b, wherein $R^7$ is an aromatic or an aliphatic group, via palladium catalyzed carbon-carbon bond formation.

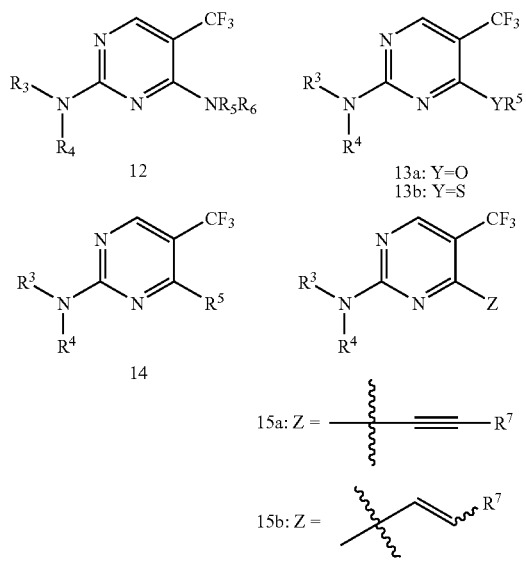

Compounds of formula 12–15 are useful for example, in the treatment of abnormal cell growth, such as cancer, in mammals. For example, compounds 12–15 are inhibitors of protein kinases. In particular, compound of formula 12 are selective inhibitors of certain receptor and non-receptor tyrosine kinases, e.g., FAK (focal adhesion kinase). Compounds such as these are described in U.S. patent application Ser. Nos. 10/734,039 and 10/733,215.

EXAMPLES

The following examples illustrate the preparation of the compounds of the present invention. NMR data are reported in parts per million and are referenced to the deuterium lock signal from the sample solvent. Commercial reagents were utilized without further purification. THF refers to tetrahydrofuran and DMF refers to N,N-dimethylformamide. Chromatography refers to column chromatography performed using 0.040 mm silica gel and executed under flash chromatography conditions. Low Resolution Mass Spectra (LRMS) were recorded on a Fisons Atmospheric Pressure Chemical Ionization platform, which uses a 50/50 mixture of acetonitrile/water with 0.1% formic acid as the ionizing agent. All non-aqueous reactions were run under a nitrogen atmosphere for convenience and to maximize yields. Concentration under reduced pressure means that a rotary evaporator was used. Aromatic or aliphatic amine nucleophiles were either purchased and used without further purification or prepared by standard methods of amine synthesis known to those skilled in the art.

Where analytical HPLC chromatography is referred to in the preparations and examples below, the general conditions used, unless otherwise indicated, are as follows. The column used is a ZORBAX RXC18 column (manufactured by Hewlett Packard) of 150 mm distance and 4.6 mm interior diameter. The samples are run on a Hewlett Packard-1100 system. A gradient solvent method is used running 100 percent ammonium acetate/acetic acid buffer (0.2 M) to 100 percent acetonitrile over 10 minutes. The system then proceeds on a wash cycle with 100 percent acetonitrile for 1.5 minutes and then 100 percent buffer solution for 3 minutes. The flow rate over this period is a constant 3 mL/minute.

Example 1

Preparation of 2,4-dichloro-5-trifluoromethylpyrimidine: 5-Trifluoromethyluracil (250 g, 1.39 mol) and phosphorous oxychloride (655 mL, 6.94 mol, 5 equiv) were charged to a 3 L 4-neck flask equipped with overhead stirrer, a reflux condenser, an addition funnel and an internal theromocouple. The contents were maintained under a nitrogen atmosphere as concentrated phosphoric acid (85 wt %, 9.5 mL, 0.1 equiv) was added in one portion to the slurry, resulting in a moderate exotherm. Diisopropylethylamine (245 mL, 1.39 mol, 1 equiv) was then added dropwise over 15 min at such a rate that the internal temperature of the reaction reached 85–90° C. by the end of the addition. By the end of the amine addition the reaction mixture was a homogenous light-orange solution. Heating was initiated and the orange solution was maintained at 100° C. for 20 h, at which time HPLC analysis of the reaction mixture indicated that the starting material was consumed. External heating was removed and the contents of the flask were cooled to 40° C. and then added dropwise to a cooled mixture of 3N HCl (5 L, 10 equiv) and diethyl ether (2 L) keeping the temperature of the quench pot between 10 and 15° C. The layers were separated, and the aqueous layer was extracted once with ether (1 L). The combined organic layers were combined, washed with water until the washes were neutral (5×1.5 L washes), dried with $MgSO_4$ and concentrated to provide 288 g (95% yield) of a light yellow-orange oil of 96% purity (HPLC). This material can be further purified by distillation (bp 109° C. at 79 mmHg).

Example 2

General Procedure for Non-Selective Amine Addition

Method A: A mixture of (2-Chloro-5-trifluoromethyl-pyrimidin-4-yl)-p-tolyl-amine (9) and (4-Chloro-5-trifluoromethyl-pyrimidin-2-yl)-p-tolyl-amine (8) To a solution of 5-trifluoromethyl-2,4-dichloropyrimidine (500 mg; 2.3 mmol) in DCE/t-butanol (20 mL) was added 4-methylaniline (247 mg; 1 eq) followed by dropwise addition triethylamine (1.1 eq). After stirring overnight the reaction was concentrated and taken up in ethyl acetate, washed with sat. $NaHCO_3$, dried over $Na_2SO_4$, and the solvent removed. Analytical HPLC analysis revealed that the crude reaction contained a 1.4:1 mixture of 8:9. The resulting mixture of isomers was separated on a Shimadzu preparative HPLC system using a standard gradient (Waters XTerra Prep MS $C_{18}$ column 5m, 50×50 mm; 0.1% $NH_4OH$ in 40–90% $ACN/H_2O$ 75 mL/min, 15 min gradient elution) to provide; (2-Chloro-5-trifluoromethyl-pyrimidin-4-yl)-p-tolyl-amine (9) (122 mg): $^1H$ NMR ($CDC_3$, 400 MHz) δ 2.35 (s, 3H), 6.99 (br s, 1H), 7.19 (d, J=8.3 Hz, 2H), 7.38 (d, J=8.3 Hz, 2H), 8.38 (s, 1H); $^{13}C$ NMR ($CDCl_3$, 100 MHz) δ 163.9, 157.6, 156.0 (q, J=5 Hz), 136.1, 133.7, 130.0, 123.8 (q, J=270 Hz), 122.8, 106.6 (q, J=32 Hz), 21.2; HPLC ret. Time: 7.236 min. LRMS (M+): 288.1, 290.1. and ((4-Chloro-5-trifluoromethyl-pyrimidin-2-yl)-p-tolyl-amine (8) (205 mg): $^1H$ NMR ($CDCl_3$, 400 MHz) 2.33 (s, 3H), 7.17 (d, J=8.3 Hz, 2H), 7.42 (d, J=8.3 Hz, 2H), 7.46 (br s, 1H), 8.52 (s, 1H); $^{13}$C NMR (CDCl$_3$, 100 MHz) 160.9, 157.6 (br), 134.9, 134.8, 129.9, 122.8 (q, J=269 Hz), 121.1, 113.7 (q, J=34 Hz), 21.1; HPLC ret. Time: 8.137 min. LRMS (M+): 288.1, 290.1. Confirmation of the structures of the two isomers was obtained by single crystal X-ray analysis.

General Procedures for Selective Addition of Amines Using a Lewis Acid

Method B: (4-Chloro-5-trifluoromethyl-pyrimidin-2-yl)-p-tolyl-amine (8). To a solution of 5-trifluoromethyl-2,4-dichloropyrimidine (2 g; 9.2 mmol) in 1:1 DCE/t-BuOH (80 mL) was added Zinc chloride (11 mL of a 1M solution in ether; 1.2 eq) at 0° C. After 1 hour, 4-methylaniline (988 mg; 1 eq) was added followed by dropwise addition of a solution of triethylamine (1.03 g; 1.1 eq) in 10 mL of DCE/t-BuOH. After stirring for 1.5 hours the reaction was concentrated. Analytical HPLC analysis revealed that the crude reaction contained <5% of isomer 9. The desired product 8 was obtained as a white solid (2.25 g; 85%) following crystallization from methanol. HPLC ret. Time: 8.169 min. LRMS (M+): 288.2, 290.1.

The application of Method B with a variety of other amines allows for the preparation of a variety of other 2-amino-4-chloro-5-trifluoromethylpyrimidines including, but not limited to those outlined below.

5-(4-Chloro-5-trifluoromethyl-pyrimdin-2-ylamino)-1,3-dihydro-indol-2-one: $^1$H NMR (DMSO-d$_6$, 400 MHz) δ 3.29 (s, 2H), 6.76 (d, J=7.9 Hz, 2H), 7.39 (d, J=8.3 Hz), 7.51 (br s, 1H), 8.71 (s, 1H), 10.33 (s, 1H), 10.49 (s, 1H). $^{13}$C NMR (DMSO-d$_6$, 100 MHz) δ 177.0, 161.3, 158.7 (br), 140.7, 132.8, 126.9, 123.7 (q, J=268 Hz), 121.0, 118.7, 111.2 (q, J=32 Hz), 109.6, 36.7; HPLC ret. time: 5.759 min. LRMS (M+) 329.1, 331.1.

(4-Chloro-5-trifluoromethyl-pyrimidin-2-yl)-(4-methoxy-phenyl)-amine: $^1$H NMR (CDCl$_3$, 400 MHz) δ 3.80 (s, 3H), 6.91 (d, J=9.1 Hz, 2H), 7.38 (br s, 1H), 7.43 (d, J=8.7 Hz, 2H), 8.50 (s, 1H); $^{13}$C NMR (CDCl$_3$, 100 MHz) δ 161.1, 157.6 (br), 157.2, 130.3, 123.2, 122.9 (q, J=269 Hz), 114.5, 113.5 (q, J=34 Hz), 112.5, 55.7; HPLC ret. time: 7.550 min. LRMS (M+) 304.2, 306.1.

(4-Chloro-5-trifluoromethyl-pyrimidin-2-yl)-(4-nitro-phenyl)-amine: $^1$H NMR (CDCl$_3$, 400 MHz) δ 7.80 (br s, 1 H), 7.82 (d, J=24 Hz, 2H), 8.26 (d, J=23 Hz, 2H), 8.67 (s, 1H); $^{13}$C NMR (DMSO-d$_6$, 100 MHz) δ 160.7, 158.9 (q, 4.5 Hz), 158.6, 145.7, 142.7, 125.6, 123.3 (q, J=269 Hz),120.0, 113.8 (q, J=34 Hz); HPLC ret. time: 7.720 min. LRMS (M+) 318.3, 320.3.

(4-Chloro-5-trifluoromethyl-pyrimidin-2-yl)-(3,4-dichloro-phenyl)-amine: $^1$H NMR (CDCl$_3$, 400 MHz) δ 7.39 (m, 3H), 7.86 (s,1H), 8.60 (s, 1H); $^{13}$C NMR (CDCl$_3$, 100 MHz) δ 160.2, 159.8, 157.6 (q, J=5 Hz), 137.2, 133.2, 130.9, 127.9, 112.6 (q, J=270 Hz), 121.9, 119.5, 115.0 (q, J=34 Hz); HPLC ret. time: 8.837 min. LRMS (M+) 342.1, 344.1.

(4-Chloro-5-trifluoromethyl-pyrimidin-2-yl)-o-tolyl-amine: $^1$H NMR (CDCl$_3$, 400 MHz) δ 2.30 (s, 3H), 7.15 (m, 2H), 7.26 (m, 3H), 7.35 (d, J=7.5 Hz, 1H), 8.51 (s, 1H); $^{13}$C NMR (CDCl$_3$, 100 MHz) δ 161.5, 159.7, 157.8 (q, J=4.5 Hz), 135.4, 131.1, 127.0, 126.3, 124.0, 122.8 (q, J=270 Hz), 113.8 (q, J=34 Hz), 18.3; HPLC ret. time: 7.663 min. LRMS (M+) 288.1, 290.1.

(3-Chloro-phenyl)-(4-chloro-5-trifluoromethyl-pyrimidin-2-yl)-amine: $^1$H NMR (CDCl$_3$, 400 MHz) δ 7.11 (d, J=9.1 Hz, 1H), 7.28 (t, J=8.1 Hz, 1H), 7.38 (brs, 1H), 7.41 (d, J=9.1 Hz, 1H), 7.75 (s, 1H), 8.59 (s, 1H); $^{13}$C NMR (CDCl$_3$, 100 MHz) δ 60.4, 159.7, 157.6 (q, J=4.5 Hz), 138.8, 135.1, 124.6, 122.6 (q, J=269 Hz), 120.4, 118.3, 114.7 (q, J=34 Hz); HPLC ret. time: 8.301 min. LRMS (M+) 308.1, 310.1.

(4-Chloro-phenyl)-(4-chloro-5-trifluoromethyl-pyrimidin-2-yl)-amine: $^1$H NMR (CDCl$_3$, 400 MHz) δ 7.33 (d, J=9.1 Hz, 2H), 7.42 (s, 1H), 7.53 (d, J=8.7 Hz, 2H), 8.56 (s, 1H); $^{13}$C NMR (CDCl$_3$, 100 MHz) δ 160.5, 159.7, 157.6 (q, J=5 Hz), 136.2, 129.8, 129.4 122.7 (q, J=270 Hz), 118.6, 114.4 (q, J=34 Hz); HPLC ret. time: 8.316 min. LRMS (M+) 308.1, 310.0.

(4-Chloro-5-trifluoromethyl-pyrimidin-2-yl)-methyl-p-tolyl-amine: $^1$H NMR (CDCl$_3$, 400 MHz) δ 2.36 (s, 3H), 3.52 (s, 3H), 7.13 (d, J=8.3 Hz, 2H), 7.23 (d, J=9.1 Hz, 2H), 8.39 (br s, 1H); $^{13}$C NMR (CDCl$_3$, 100 MHz) δ 162.4, 159.1, 157.2, 141.3, 137.3, 130.4, 126.4, 123.2 (q, J=269 Hz), 111.7 (q, J=34 Hz), 39.6, 21.4; HPLC ret. time: 8.708 min. LRMS (M+) 302.2, 304.1.

(4-Chloro-5-trifluoromethyl-pyrimidin-2-yl)-(3-oxazol-5-yl-phenyl)-amine: $^1$H NMR (DMSO-d$_6$, 400 MHz) δ 7.44 (m, 2H), 7.63 (s, 1H), 7.65 (m, 1H), 8.07 (s, 1H), 8.44 (s, 1H), 8.82 (s, 1H), 10.78 (s, 1H); $^{13}$C NMR (DMSO-d$_6$, 100 MHz) δ 161.2, 158.9 (br), 158.4, 152.6, 151.0, 139.8, 130.2, 128.5, 123.6 (q, J=269 Hz), 122.9, 121.2, 120.1, 116.4, 112.3 (q, J=34 Hz); HPLC ret. time: 7.374 min. LRMS (M+) 341.2, 343.1.

4-(4-Chloro-5-trifluoromethyl-pyrimidin-2-ylamino)-benzamide: $^1$H NMR (DMSO-d$_6$, 400 MHz) δ 7.26 (s, 1H), 7.74 (d, J=8.7 Hz, 2H), 7.83 (d, J=9.1 Hz, 2H), 8.44 (br s, 1H), 8.84 (s, 1H), 10.87 (s, 1H); $^{13}$C NMR (DMSO-d$_6$, 100 MHz) δ 168.0, 161.0, 158.9 (br), 158.4, 141.8, 129.6, 129.0, 123.5 (q, J=268 Hz), 119.9, 112.6 (q, J=34 Hz); HPLC ret. time: 5.605 min. LRMS (M+) 317.1, 319.3.

(4-Chloro-5-trifluoromethyl-pyrimidin-2-yl)-(4-methanesulfonyl-phenyl)-amine: $^1$H NMR (DMSO-d$_6$, 400 MHz) δ 3.15 (s, 3H), 7.87 (d, J=8.7 Hz, 2H), 7.93 (d, J=8.7 Hz, 2H), 8.89 (s, 1H), 11.10 (s, 1H); $^{13}$C NMR (DMSO-d$_6$, 100 MHz) δ 60.9, 158.9 (br), 158.5, 143.9, 135.3, 128.8, 123.4 (q, J=269 Hz), 120.4, 113.3 (q, J=34 Hz), 44.5; HPLC ret. time: 6.542 min. LRMS (M+) 352.1, 354.1.

4-(4-Chloro-5-trifluoromethyl-pyrimidin-2-ylamino)-benzenesulfonamide: $^1$H NMR (DMSO-d$_6$, 400 MHz) δ 7.25 (s, 2H), 7.76 (d, J=9.1 Hz, 2H), 7.83 (d, J=9.1, 2H), 8.85 (s, 1H), 10.98 (s, 1H); $^{13}$C NMR (DMSO-d$_6$, 100 MHz) δ 161.0, 158.9 (br), 158.5, 142.2, 139.2, 127.3, 123.5 (q, J=269 Hz), 120.3, 113.0 (q, J=33 Hz); HPLC ret. time: 5.983 min. LRMS (M+) 353.2, 355.2.

For those cases in which the amine nucleophile is aliphatic or is an aromatic amine capable of serving as a multidentate ligand for the Lewis Acid, additional equivalents of Lewis Acid are necessary for the reaction to proceed selectively.

Method C: N-(4-Chloro-5-trifluoromethyl-pyrimidin-2-yl)-N',N'-dimethyl-benzene-1,4-diamine: To a solution of 5-trifluoromethyl-2,4-dichloropyrimidine (500 mg; 2.3 mmol) in 1:1 DCE/t-BuOH (20 mL) was added Zinc chloride (5.1 mL of a 1 M solution in ether; 2.2 eq) at 0° C. After 1 hour, N,N-dimethyl-1,4-phenylenediamine (313 mg; 1 eq) was added followed by dropwise addition of a solution of triethylamine (279 mg; 1.1 eq) in 5 mL of DCE/t-BuOH. After stirring for 24 hours the reaction was concentrated. The product was obtained as a pale green solid (531 mg; 73%) following crystallization from 25% H$_2$O/methanol. $^1$H NMR (DMSO-d$_6$, 400 MHz) δ 2.83 (s, 6H), 6.69 (m, 2H), 7.39 (m, 2H), 8.65 (s, 1H), 10.32 (s, 1H); $^{13}$C NMR (CDCl$_3$, 100 MHz) δ 161.3, 158.8 (br), 158.5 (br), 148.3, 128.2, 123.8 (q, J=268 Hz), 123.0, 113.1, 110.8 (br), 41.0; HPLC ret. time: 7.901 min. LRMS (M+) 317.3, 319.3.

The application of Method C with a variety of other amines allows for the preparation of a variety of other 2-amino-4-chloro-5-trifluoromethylpyrimidines including, but not limited to those outlined below.

(4-Chloro-5-trifluoromethyl-pyrimidin-2-yl)-(2-methoxy-phenyl)-amine: $^1$H NMR (CDCl$_3$, 400 MHz) δ 3.90 (s, 3H), 6.91 (d, J=8.1 Hz, 1H), 7.01 (m, 1H), 7.07 (m, 1H), 8.09 (s, 1H), 8.38 (d, J=7.9 Hz, 1H), 8.57 (s, 1H); $^{13}$C NMR (CDCl$_3$, 100 MHz) δ 160.4, 159.3, 157.5 (q, J=4.5 Hz), 148.6, 127.4, 124.1, 122.9 (q, J=269 Hz), 121.1, 119.8, 113.7 (q, J=34 Hz), 110.4, 56.0; HPLC ret. time: 8.151 min. LRMS (M+) 304.2, 306.2.

(4-Chloro-5-trifluoromethyl-pyrimidin-2-yl)-(4-methylbenzyl)-amine: $^1$H NMR (DMSO-d$_6$, 400 MHz) δ 2.23 (s, 3H), 4.46 (m, 2H), 7.09 (m, 2H), 7.15 (m, 2H), 8.57 (2s, 1H), 8.98 (m, 1 H); HPLC ret. time: 8.238 min. LRMS (M+) 302.0, 304.0.

(4-Chloro-5-trifluoromethyl-pyrimidin-2-yl)-cyclohexyl-amine: $^1$H NMR (DMSO-d$_6$, 400 MHz) δ 1.10 (m, 1H), 1.23 (m, 4H), 1.55 (m, 1H), 1.65 (m, 2H), 1.81 (m, 2H), 3.69 (m, 2H), 8.47 (m, 1H), 8.55 (2 br s, 1H); HPLC ret. time: 8.548 min. LRMS (M+) 280.1, 282.1.

(4-Chloro-5-trifluoromethyl-pyrimidin-2-yl)-cyclohexylmethyl-amine: $^1$H NMR (DMSO-d$_6$, 400 MHz) δ 0.86 (m, 2H), 1.11 (m, 3H), 1.50 (m,1H), 1.58 (m, 1H), 1.64 (m, 4H), 3.12 (m, 2H), 8.55 (m, 2H); HPLC ret. time: 9.039 min. LRMS (M+) 294.1, 296.1.

4-Chloro-2-piperidin-1-yl-5-trifluoromethyl-pyrimidine $^1$H NMR (CDCl$_3$-d$_6$, 400 MHz) δ 1.60 (m, 4H), 1.68 (m, 2H), 3.82 (m, 4H), 8.36 (s, 1H); $^{13}$C NMR (DMSO-d$_6$, 100 MHz) δ 161.5, 159.1, 157.2 (q, J=4.5 Hz), 123.4 (q, J=268 Hz), 109.8 (q, J=34 Hz), 45.4, 25.9, 24.7; HPLC ret. time: 8.915 min. LRMS (M+) 266.1, 268.2.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

All patents, applications, publications, test methods, literature, and other materials cited herein are hereby incorporated herein by reference in their entireties.

The invention claimed is:

1. A method of making a compound of the formula

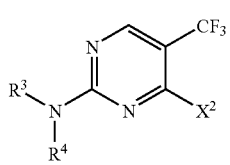

11 wherein X$^2$ is a leaving group, and R$^3$ and R$^4$ are substituents independently selected from the group consisting of hydrogen, an aromatic group and an aliphatic group; or taken together —NR$^3$R$^4$ can form a 4–11 membered aromatic or aliphatic ring; wherein the method comprises reacting a compound of formula 10

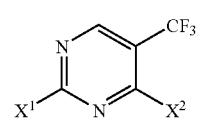

10 with an amine of formula 3 (HNR$^3$R$^4$) in the presence of a Lewis Acid and a non-nucleophilic base to form a compound of formula 11, wherein X$^1$ is a leaving group.

2. A method of claim 1 wherein X$^1$ and X$^2$ are the same or different leaving groups independently selected from the group consisting of halide, arylsulfonate, alkylsulfonate, perfluoroalkylsulfonate, arylsulfinate or alkylsulfinate.

3. A method of claim 2 wherein X$^1$ and X$^2$ are the same or different and are each independently halides.

4. A method of claim 3 wherein X$^1$ and X$^2$ are chloride.

5. A method of claim 1 wherein said amine, HNR$^3$R$^4$, is an aromatic amine and 0.25–10 equivalents of Lewis Acid are used relative to the amount of pyrimidine 10.

6. A method of claim 1 wherein said amine, HNR$^3$R$^4$, is an aromatic amine and 0.5–3 equivalents of Lewis Acid are used relative to the amount of pyrimidine 10.

7. A method of claim 5 wherein the Lewis Acid is a salt of a metal ion selected from the group consisting of Zn, Mg, Sn, Ti, Al, B, Li, Ag, and Cu.

8. A method of claim 7 wherein said Lewis Acid is a salt of Zn or Mg.

9. A method of claim 7 wherein said Lewis Acid is ZnCl$_2$.

10. A method of claim 1 wherein said amine, HNR$^3$R$^4$, is an aliphatic amine or is an aromatic amine capable of serving as a multidentate ligand for the Lewis Acid and 0.5–10 equivalents of Lewis Acid are used relative to the amount of pyrimidine 10.

11. A method of claim 1 wherein said amine, HNR$^3$R$^4$, is an aliphatic amine or is an aromatic amine capable of serving as a multidentate ligand for the Lewis Acid and 1–4 equivalents of Lewis Acid are used relative to the amount of pyrimidine 10.

12. A method of claim 10 wherein the Lewis Acid is a salt of a metal ion selected from the group consisting of Zn, Mg, Sn, Ti, Al, B, Li, Ag, and Cu.

13. A method of claim 12 wherein said Lewis acid is a salt of Zn or Mg.

14. A method of claim 12 wherein said Lewis Acid is ZnCl$_2$.

* * * * *